United States Patent [19]

Scott

[11] Patent Number: 5,407,877
[45] Date of Patent: Apr. 18, 1995

[54] CATALYST TREATMENT PROCESS

[75] Inventor: John D. Scott, Nr. Northwich, England

[73] Assignee: Imperial Chemical Industries PLC, London, England

[21] Appl. No.: 984,449

[22] Filed: Dec. 2, 1992

[30] Foreign Application Priority Data

Dec. 3, 1991 [GB] United Kingdom ................ 9125678

[51] Int. Cl.$^6$ .......................... B01J 27/32; B01J 38/46
[52] U.S. Cl. ........................................ 502/36; 502/37; 502/55; 570/168; 570/169
[58] Field of Search ..................... 502/55, 51, 50, 36, 502/34, 38

[56]  References Cited

U.S. PATENT DOCUMENTS

| | | | |
|---|---|---|---|
| 2,546,031 | 3/1951 | Hanson | 502/51 |
| 2,745,886 | 5/1956 | Ruh et al. | 502/228 |
| 2,937,210 | 5/1960 | Pearotti et al. | 502/55 |
| 3,431,067 | 3/1969 | Kato et al. | 570/168 |
| 3,435,086 | 3/1969 | Soderquist et al. | 260/669 |
| 3,455,840 | 7/1969 | Kato et al. | 570/168 |
| 4,139,568 | 2/1979 | Baugh et al. | 260/653.7 |
| 4,145,311 | 3/1979 | von Halasz et al. | 252/415 |
| 4,147,733 | 4/1979 | Fiske et al. | 260/653.4 |
| 4,694,112 | 9/1987 | Willenberg et al. | 568/842 |
| 5,227,350 | 7/1993 | Scott et al. | 502/36 |

FOREIGN PATENT DOCUMENTS 0475693  3/1992  European Pat. Off. ............. 502/36

Primary Examiner—Asok Pal
Attorney, Agent, or Firm—Cushman Darby & Cushman

[57]  ABSTRACT

A process for the reactivation of a chromium-based fluorination catalyst, in particular chromia, by contacting the deactivated chromium-based fluorination catalyst with an atmosphere containing water vapour at elevated temperature, preferably above 300° C.

9 Claims, No Drawings

CATALYST TREATMENT PROCESS

This invention relates to a process for the reactivation of a deactivated chromium based fluorination catalyst and to a process for the production of hydrofluorocarbons by the fluorination of hydrocarbons or hydrohalocarbons, in particular a process for the production of 1,1,1,2-tetrafluoroethane by the fluorination of 1-chloro-2,2,2-tetrafluoroethane with hydrogen fluoride, in the presence of a reactivated chromium based fluorination catalyst.

The production of fluorinated hydrocarbons, which may also contain halogen atoms other than fluorine, by the catalysed vapour-phase fluorination of hydrocarbons and halogenated hydrocarbons with hydrogen fluoride is well known and numerous catalysts have been proposed for use in such processes. Catalysts comprising or based upon chromium are frequently employed in these known processes. The chromium based catalyst may for example be chromium oxide, commonly known as chromia, or it may be a halogenated chromia, for example a chromium fluoride or oxyfluoride. Furthermore, these chromium based catalysts may also comprise amounts of other species which are present in order to promote the activity of the catalyst, for example the chromium based catalyst may also comprise activaty promoting amounts of zinc, nickel, cobalt or other metals.

As examples of vapour phase fluorination processes in which chromium based catalysts are employed may be mentioned inter alia, the reaction of trichloroethylene with hydrogen fluoride to produce 1-chloro-2,2,2-trifluoroethane as described in GB 1,307,224, the reaction of 1-chloro-2,2,2-trifluoroethane with hydrogen fluoride to produce 1,1,1,2-tetrafluoroethane as described in GB 1,589,924 and the fluorination of chlorodifluoroethylene to 1-chloro-2,2,2-trifluoroethane as is also described for the removal of chlorodifluoroethylene impurity from 1,1,1,2-tetrafluoroethane in GB 1,589,924.

The use of such catalysts in these processes does however suffer from the problem that the catalyst is deactivated with time so that the activity of the catalyst, reflected in the reactant conversion, and selectivity of the catalyst, decrease gradually with time. The loss in activity may be reduced to a certain extent by steadily increasing the temperature at which the reaction is carried out. However, such increase in temperature leads inevitably to a consequential decrease in the selectivity of the process.

It is conventional practice for the catalyst to be periodically "re-activated" or "regenerated". This re-activation of the catalyst is conventionally carried out by heating the catalyst in oxygen or air in order to remove carbon which is deposited upon the catalyst surface. However, such re-activation is not wholly adequate, and the catalyst may, despite such reactivation, still operate with a decreased activity and selectivity. Furthermore, since the re-activation is not 100% so that a higher temperature, and consequently lower selectivity, must be used after each re-activation in order to achieve the initial catalyst activity, the catalyst may only be re-activated by this process a finite number of times after which the catalyst would hitherto have been disposed of and replaced with fresh catalysts. The cost of such catalyst replacement may be high. It is desirable that satisfactory catalyst activity and selectivity are maintained for as long as possible.

We have now found that the activity and selectivity of deactivated chromium based fluorination catalysts may be substantially restored and the effective active lifetime of the catalyst may be increased if the chromium based catalyst is contacted with water vapour.

According to a first aspect of the present invention there is provided a process for the reactivation of a deactivated chromium based fluorination catalyst which comprises contacting the deactivated catalyst with an atmosphere comprising water vapour at an elevated temperature.

By "reactivation" of a deactivated chromium based catalyst there is meant a process which is suitable for restoring, at least to a greater extent than was possible by known reactivation techniques, to a deactivated catalyst the activity and selectivity with which the initial catalyst could be operated.

The deactivated catalyst which is re-activated by the process of the invention may have previously been subjected to one or more reactivations with oxygen or air, to remove carbon deposited on the catalyst surface, prior to the reactivation process of the invention. Usually the deactivated catalyst which is reactivated according to the invention will be deactivated to such an extent that re-activation with oxygen or air is no longer sufficient to restore an acceptable level of activity to the catalyst.

The catalyst may be referred to as deactivated when it has been employed as a fluorination catalyst for such a time that the absolute conversion of the reaction in which it is being employed at the particular operating conditions employed has dropped by at least about 5% conversion, especially by at least about 10% conversion, although the catalyst may be referred to as deactivated after much shorter or longer periods of operation.

Chromium based fluorination catalysts are typically based more specifically upon chromia. The chromia may be for example fluorinated so that the fluorination catalyst may be a chromium oxyfluoride species. Furthermore the chromia may comprise activatity prooting amounts of metals, for example zinc, nickel or cobalt.

The chromia based catalyst may be supported on a support system. The support system may be, for example a metal oxide, for example alumina ($Al_2O_3$), magnesia (MgO), a metal fluoride, for example aluminium fluoride and magnesium fluoride or the support system may be an activated carbon.

The active catalytic species, for example chromia-based, may be generated in situ so that for example a source of chromium may be employed as the catalyst which under the reaction conditions is converted to chromia or a chromia based species. Thus, for example an aqueous salt of chromium, for example chromium nitrate, may be employed which under the reaction conditions is converted to chromia.

The process of the invention is suitable for the reactivation of all chromium based fluorination catalysts, and in particular fluorination catalysts based upon chromia.

The re-activation process is preferably carried out in the substantial absence of the hydrocarbon or halogenated hydrocarbon substrate of the reaction in which the catalyst is being employed. Indeed the presence of the hydrocarbon or halogenated hydrocarbon substrate during the re-activation process may have a deleterious effect on the activity of the catalyst.

Further, the reactivation process is preferably carried out in the substantial absence of hydrogen fluoride. Thus, the atmosphere with which the de-activated catalyst is contacted preferably contains less than 15% by weight hydrogen fluoride, more preferably less than 10% by weight and especially less than 5% by weight hydrogen fluoride. We especially prefer to employ an atmosphere which comprises as little hydrogen fluoride as possible other than any hydrogen fluoride which may be evolved during the re-activation process of the invention.

The reactivation may be carried out on the catalyst in the fluorination reactor, i.e. in situ, in which case the hydrocarbon or halogenated hydrocarbon and hydrogen fluoride feeds are preferably temporarily stopped whilst the reactivation process according to the invention is carried out. Alternatively, the re-activation process may be carried out in a separate "re-activation vessel" to which the deactivated catalyst is transferred from the fluorination reactor vessel.

Following the re-activation process of the invention, the catalyst may be contacted with hydrogen fluoride at elevated temperature, for example temperatures in the range from about 150° C. to about 450° C., prior to its further use in catalysing a fluorination reaction.

The temperature at which the deactivated catalyst is contacted with the atmosphere comprising water vapour is such that the water is in the vapour phase and the temperature is preferably at least 300° C., more preferably at least 350° C. The temperature need be no hither than about 500° C. although hither temperatures, say up to about 700° C. may be employed if desired.

Autogenous pressures are conveniently employed, although subatmospheric or superatmospheric pressures may be employed if desired. Thus, the pressure may be for example within the range from about 0.1bar to about 50 bar.

The water vapour may be passed over the catalyst in conjunction with an inert diluent, for example nitrogen, carbon dioxide, helium or argon. Furthermore the water vapour may be passed over the catalyst in conjunction with oxygen or air, which may be used in addition to or instead of the inert diluent. We prefer that at least some oxygen or air is employed since the presence of oxygen or air allows the reactivation process of the invention to be combined with the conventional treatment process in which the catalyst is heated in oxygen or air.

The water vapour concentration in the atmosphere which is contacted with the catalyst may vary within a wide range, indeed a pure water vapour atmosphere may be contacted with the catalyst. However, in order to prevent condensation of water in downstream equipment when the treatment is effected on the catalyst in the fluorination reactor, we generally prefer that the water vapour concentration is from about 0.1% v/v, to about 10% v/v, and preferably from about 1% v/v to about 5% v/v. A water vapour concentration of 2.3% v/v corresponds to a saturated air/water vapour stream at room temperature and pressure.

The contact time between the water vapour and the catalyst may also vary within wide limits but typically is in the range from about 1 second to about 100 seconds. Contact times greater than 100 seconds may be employed if desired although we prefer that the contact time is as small as possible whilst giving effective reactivation in order that the time for which the reactor is being used for reactivation rather than the fluorination reaction is as small as possible.

The time required to achieve effective reactivation of the deactivated catalyst depends upon the contact time, water concentration and reactivation temperature, as well as the particular catalyst and the fluorination reaction in which it is to be employed. Effective reactivation may be achieved, for example, in about 5 hours using a temperature of 400° C., a contact time of 2 seconds and a water concentration of 2.3% v/v. However, for the effective reactivation of chromium-based catalysts for use in commercial scale fluorination reactors, longer reactivation times, for example about 24 hours or longer, may be employed.

A further aspect of the invention resides in the use of a chromium-based fluorination catalyst which has been re-activated according to the first aspect of the invention, in fluorination processes comprising reaction of a hydrocarbon or halogenated hydrocarbon with hydrogen fluoride in the vapour phase. Halogenated alkenes or alkanes of 1–4 C atoms, preferably containing at least one chlorine atom, may be fluorinated and examples of specific fluorinations which may be effected are the production of 1,1,1,2-tetrefluoroethane from 1-chloro-2,2,2-trifluoroethane, the production of 1-chloro-2,2,2-trifluoroethane from trichloroethylene and the conversion of 1-chloro-2,2,-difluoroethylene to 1-chloro-2,2,2-trifluoroethane. Examples of other reactions in which the reactivated catalyst is useful are the reaction of perchloroethylene with hydrogen fluoride in the vapour phase to produce dichlorotrifluoroethane (123), chlorotetrafluoroethane (124) and/or pentafluoroethane (128), and the reaction of perchloroethylene with chlorine and hydrogen fluoride in the vapour phase to produce trichlorotrifluoroethane (113), dichlorotetrafluoroethane (114/114a) and/or chloropentafluoroethane.

The fluorination conditions may be those known to be usable when employing chromium based catalysts, for example atmospheric or superatmospheric pressure, hydrogen fluoride and temperatures in the range of from about 180° C. to about 500° C. depending upon the particular fluorination reaction being carried out.

The reactivation process of the first aspect of the invention is however particularly useful for the reactivation of deactivated catalysts employed in the production of 1,1,1,2-tetrafluoroethane from 1-chloro-2,2,2-trifluoroethane since we have found that use of a catalyst which has been reactivated according to the first aspect of the invention in this fluorination reaction achieves a greater selectivity to 1,1,1,2-tetrafluoroethane and in particular a greater selectivity after reactivation, than chromium based catalysts reactivated by conventional reactivation techniques.

According to a preferred embodiment of this further aspect of the invention there is provided a process for the production of 1,1,1,2-tetrafluoroethane which comprises reacting 1-chloro-2,2,2-trifluoroethane with hydrogen fluoride in the vapour phase in the presence of a catalyst which has been reactivated by a process according to the first aspect of the invention. This fluorination process may be carried out at a temperature of from about 280° C. to about 500° C.

According to a further preferred embodiment of the invention there is provided a process for the production of 1,1,1,2-tetrafluoroethane which comprises reacting 1-chloro-2,2,2-trifluoroethane with hydrogen fluoride in the vapour phase in the presence of a chromium based fluorination catalyst in which the catalyst is periodically reactivated by the process according to the first aspect of the invention. In this further preferred embodiment of the invention, the periodic treatments are preferably carried out in the substantial absence of 1-chloro-2,2,2-trifluoroethane and preferably also in the absence of hydrogen fluoride.

The frequency with which the reactivation is carried out will depend, at least some extent, upon the particular chromium based catalyst which is employed and the rate of deactivation of the catalyst during the fluorination reaction. Typically however, the catalyst may be reactivated according to the first aspect of the invention with a frequency of from about once every 100 hours of operation in a fluorination reaction to about once every 5000 hours of operation. It will not usually be necessary to re-activate the catalyst by the process of the invention until after about 500 hours of operation of the catalyst in a fluorination reaction.

The process of the preferred embodiment of the invention may be one stage of a two or three stage process, for example it may be the second stage of a process for the production of 1,1,1,2-tetrafluoroethane from trichloroethylene, the first stage being the vapour-phase fluorination of trichloroethylene with hydrogen fluoride in the presence of a chromium based fluorination catalyst. The reactivation process of the first aspect of the invention may be employed to reactivate the catalyst employed in the first stage of the process as well as the second stage of the process. Typical reaction conditions for the first stage are atmospheric or superatmospheric pressure and a temperature in the range from about 180° C. to about 300° C.

The production of 1,1,1,2-tetrafluoroethane from 1-chloro-2,2,2-trifluoroethane results in a product stream containing the toxic impurity 1-chloro-2,2,-difluoroethylene. This impurity may be removed by reacting it with hydrogen fluoride in the vapour phase in the presence of a chromium based catalyst at a temperature below 270° C., for example 150° C. to 270° C. The re-activation process of the first aspect of the invention may be employed to periodically reactivate the catalyst employed in this removal process, thus providing a three-stage process for the preparation of 1,1,1,2-tetrafluoroethane essentially free from 1-chloro-2,2-difluoroethylene from trichloroethylene using a fluorination catalyst in each of the three recation stages which may be re-activated by the process of the first aspect of the invention.

A particularly preferred embodiment of the above-described two-stage process for preparing 1,1,1,2-tetrafluoroethane from trichloroethylene comprises the steps of:

(A) contacting a mixture of 1-chloro-2,2,2-trifluoroethane and hydrogen fluoride with a chromium based fluorination catalyst at a temperature in the range from about 280° C. to about 450° C. in a first reaction zone to form a product containing 1,1,1,2-tetrafluoroethane and hydrogen chloride together with unreacted starting materials, (B) passing product of step A together with trichloroethylene to a second reaction zone containing a chromium based fluorination catalyst at a temperature in the range from about 200° C. to about 400° C. but lower than the temperature in step A to form a product containing 1-chloro-2,2,2-trifluoroethane, 1,1,1,2-tetrafluoroethane, hydrogen chloride and unreacted trichloroethylene and hydrogen fluoride;

(C) treating product of step B to separate hydrogen chloride and 1,1,1,2-tetrafluoroethane from 1-chloro-2,2,2-trifluoroethane, unreacted hydrogen fluoride and unreacted trichloroethylene, and (D) feeding 1-chloro-2,2,2-trifluoroethane obtained from step C together with hydrogen fluoride to said first reaction zone (step A), in which the chromium based catalysts employed in the first and second reaction zones are periodically reactivated by the process according to the first aspect of the invention. The catalysts in reaction zones one and two are conveniently reactivated according to the process of the first aspect of the invention at the same time although they may be reactivated separately, if desired.

At least the stoichiometric amount of hydrogen fluoride is usually employed in step A of this preferred embodiment. Typical amounts include from 2 to 10 moles, and preferably from 2 to 6 moles, of hydrogen fluoride per mole of 1-chloro-2,2,2-trifluoroethane. Accordingly, the product of this reaction step will usually contain unreacted hydrogen fluoride in addition to 1,1,1,2-tetrafluoroethane, hydrogen chloride and by-products. Preferred reaction temperatures for this stage of the process are in the range from 325° C. to 385° C. with contact times of from 1 to 100 and preferably from 5 to 30 seconds at 5 to 20 bars pressure.

From 10 to 100, preferably from 15 to 60, moles of hydrogen fluoride per mole of trichloroethylene are typically employed in step B. Again the reaction product of this stage will normally contain unreacted hydrogen fluoride. Contact times of 1 to 100 seconds, preferably 5 to 30 seconds may be used, typically at 220°–350° C. and 5 to 20 bars pressure.

As described previously, it is preferred that the reactivation process of the first aspect of the invention is carried out with water vapour and oxygen or air in order that the conventional reactivation process for removing carbon deposited on the catalyst surface may take pace at the same time as the reactivation process of the invention, thus reducing the need for a separate reactivation in which the catalyst is reactivated by contact with oxygen or air. However such separate reactivation may be necessary if removal of carbon from the catalyst surface is required at more frequent intervals than the reactivation according to the invention. The feeding of air to the catalyst during operation of the fluorination process may counter the need for separate reactivation of the catalyst with oxygen or air or at least reduce the frequency with which such conventional reactivation treatments are required.

The invention is illustrated but in no way limited by the following examples.

EXAMPLES 1 TO 4

6 g of a chromia fluorination catalyst which had been operated for over 2000 hours was divided into three equal portions.

EXAMPLE 1

A first 2 g batch of the deactivated chromia fluorination catalyst was charged into a ¼″ diameter microreactor and the microreactor was heated to 360° C. The reactor was then fed with 20 mls/minute of hydrogen fluoride for 30 minutes. 5.7 mls per minute of 1-chloro-2,2,2-trifluoroethane were then introduced into the hydrogen fluoride feed stream to make a mixed gas feed of molar ratio 3.5:1 hydrogen fluoride:1-chloro-2,2,2-trifluoroethane and give a contact time of 1.6 seconds under the reaction conditions. The product stream leaving the reactor was scrubbed with water to remove hydrogen fluoride and the organic products were quantified. The product analyses were measured over a 2.5 hour period and the results are shown in Table 1.

EXAMPLE 2

Moisture was then added to the feed to the reactor using a 1ml/minute nitrogen feed saturated in water vapour at a temperature of 20° C. The mixed feed containing about 900 ppm of water was then fed to the reactor system as described above. The results are shown in Table 1.

EXAMPLE 3

The catalyst of example 2 was replaced by a second 2 g batch of the deactivated chromia catalyst. The catalyst was heated to 400° C. and 20 mls per minute of moist nitrogen containing about 2.3 v/v water was passed over the catalyst for 2 hours. The catalyst was then cooled to 360° C. and the catalyst tested under the conditions described in example 1. The results are shown in Table 1.

EXAMPLE 4

The catalyst in example 3 was replaced by a third 2 g batch of the deactivated chromia catalyst. The catalyst was then heated to 300° C. and 20 mls per minute of moist nitrogen containing approximately 2.6% v/v water was passed over the catalyst for 2 hours. The catalyst was then heated to 360° C. and the catalyst tested under the conditions described in example 1. The results are shown in Table 1 in which the molar yield of 134a is based upon the molar amount of 1-chloro-2,2,2-trifluoroethane charged to the reactor and reaction selectivities are based upon % by volume (i.e.molar yields) of products.

TABLE 1

| EXAMPLE. | YIELD % 134a. $CF_3CH_2F$ | REACTION SELECTIVITIES | | | |
|---|---|---|---|---|---|
| | | % 134a $CF_3CH_2F$ | % 143a $CF_3CH_3$ | % 1122 $CF_2CHCl$ | % 123 $CF_3CHCl_2$ |
| 1 | 1.46 | 58.06 | 10.42 | 21.58 | 9.94 |
| 2 | 1.17 | 50.09 | 12.82 | 24.46 | 12.64 |
| 3 | 13.34 | 92.08 | 2.09 | 3.38 | 2.45 |
| 4 | 1.45 | 60.78 | 8.83 | 21.50 | 8.88 |

EXAMPLES 5 AND 6

In examples 5 and 6 a deactivated chromia catalyst, discharged after 10 weeks of operation in a fluorination reactor in which 1,1,1,2-tetrafluoroethane was produced from 1-chloro-2,2,2-trifluoroethane, was employed.

EXAMPLE 5

2 g of the above deactivated chromia catalyst was tested directly for activity as described in example 1 except that the catalyst temperature was 350° C. The results are shown in Table 2.

EXAMPLE 6

A second 2 g sample was treated with moist nitrogen as described in example 3 and tested for activity as described in example 3 except that the catalyst temperature was 350° C. The results are shown in Table 2.

TABLE 2

| EXAMPLE. | YIELD % 134a. $CF_3CH_2F$ | REACTION SELECTIVITIES | | | |
|---|---|---|---|---|---|
| | | % 134a $CF_3CH_2F$ | % 143a $CF_3CH_3$ | % 1122 $CF_2CHCl$ | % 123 $CF_3CHCl_2$ |
| 5 | 9.75 | 95.26 | 0.27 | 3.44 | 1.02 |
| 6 | 14.10 | 96.60 | 0.18 | 2.28 | 0.66 |

EXAMPLES 7 AND 8

In examples 7 and 8 a deactivated chromia catalyst, discharged after 4 weeks of operation in a fluorination reactor in which 1,1,1,2-tetrafluoroethane produced from 1-chloro-2,2,2-trifluoroethane, was employed.

EXAMPLE 7

2 g of the above deactivated chromia catalyst was tested directly for activity as described in example 1 except that the catalyst temperature was 330° C. The results are shown in Table 3.

EXAMPLE 8

A second 2 g sample was treated with moist nitrogen as described in example 3 and tested for activity as described in example 3 except that the catalyst temperature was 330° C. The results are shown in Table 3.

TABLE 3

| EXAMPLE. | YIELD % 134a. $CF_3CH_2F$ | REACTION SELECTIVITIES | | | |
|---|---|---|---|---|---|
| | | % 134a $CF_3CH_2F$ | % 143a $CF_3CH_3$ | % 1122 $CF_2CHCl$ | % 123 $CF_3CHCl_2$ |
| 7 | 15.81 | 98.78 | 0.17 | 0.85 | 0.20 |
| 8 | 18.67 | 98.99 | 0.20 | 0.58 | 0.23 |

I claim:

1. A process for the reactivation of a deactivated chromium-containing fluorination catalyst which has been used in vapor phase fluorination of a halohydrocarbon with hydrogen fluoride, which comprises contacting the deactivated chromium-containing fluorination catalyst with an atmosphere comprising at least about 0.1% v/v water vapour and less than 15% by weight hydrogen fluoride at a temperature greater than about 300° C. and up to 500° C. for a time sufficient to increase the activity of the catalyst.

2. A process as claimed in claim 1 in which the atmosphere comprises less than 10% by weight hydrogen fluoride.

3. A process as claimed in claim 1 in which the contact temperature is at least 350° C.

4. A process as claimed in claim 3 in which the atmosphere comprises from about 0.1% by volume to 10% by volume water vapour.

5. A process as claimed in claim 4 in which the atmosphere comprises from about 1% by volume to about 5% by volume water vapour.

6. A process as claimed in claim 1 in which the atmosphere further comprises air or oxygen as an oxidising agent.

7. A process as claimed in claim 6 in which the oxidising agent is air.

8. A process as claimed in claim 1 wherein the catalyst is a chromia-containing fluorination catalyst and said catalyst is contacted at a temperature of at least 350° C. with nitrogen gas containing from about 0.1% to 10% by volume of water vapor in the substantial absence of hydrocarbon and halogenated hydrocarbon, said contact being carried out by passing the gas containing water vapor over the catalyst until the catalyst is reactivated.

9. A process as claimed in claim 1 wherein the deactivated chromium-containing fluorination catalyst comprises chromia or halogenated chromia which been deactivated by use in the vapour phase fluorination of a hydrocarbon or halogenated hydrocarbon.

* * * * *